United States Patent [19]

Kaakinen

[11] Patent Number: 5,253,514

[45] Date of Patent: Oct. 19, 1993

[54] WATER-BORNE PARTICULATE-MEASURING APPARATUS

[76] Inventor: John W. Kaakinen, 4131 N. Overlook Ter., Portland, Oreg. 97217

[21] Appl. No.: 800,994

[22] Filed: Dec. 2, 1991

[51] Int. Cl.$^5$ ............................................. G01N 15/06
[52] U.S. Cl. ................................................... 73/61.73
[58] Field of Search ................. 73/61.63, 61.64, 61.71, 73/61.72, 61.73, 64.56, 863.23, 863.83, 864.34

[56] References Cited

U.S. PATENT DOCUMENTS

| | | | |
|---|---|---|---|
| 4,341,124 | 7/1982 | Rodgers et al. | 73/863.23 |
| 4,554,822 | 11/1985 | Eisenhauer et al. | 73/61 |
| 4,583,396 | 4/1986 | Hunt et al. | 73/61.73 |
| 4,765,963 | 8/1988 | Mukogawa et al. | 73/61.71 |
| 4,786,473 | 11/1988 | Mukogawa et al. | 73/61 |

Primary Examiner—Robert Raevis
Attorney, Agent, or Firm—Chernoff, Vilhauer, McClung & Stenzel

[57] ABSTRACT

Apparatus for measuring, on an automated and batch basis, the fouling potential of larger particulate-containing feed water is disclosed.

5 Claims, 4 Drawing Sheets

WATER-BORNE PARTICULATE-MEASURING APPARATUS

The government has a non-exclusive, royalty-free license to practice this invention under Contract No. DAAK70-89-C-0019 awarded by The U.S. Army.

BACKGROUND OF THE INVENTION

Given the increasing number of dramatic shortfalls in water supply, increasing usage of reverse osmosis (RO) to desalinate salt and brackish water has been made. In order for RO to be efficient, pretreatment of the feed water by processes such as filtration or clarification to remove particulate matter is typically necessary to prevent fouling of RO equipment, especially when the feed source is surface water. In order to determine the fouling potential of such water and the degree of pretreatment necessary to control RO fouling, the level of particulate matter in the feed water needs to be checked frequently. Such particulate level monitoring is conventionally done by an ASTM-specified manual test comprising measuring the rate of plugging of a 0.45 micron (micrometer) pore size membrane filter at 30 psi and calculating the plugging factor (PF) or silt density index (SDI) from the values obtained. However, this conventional manual method has a number of disadvantages. The method is time-consuming, requiring 30 minutes or more per analysis, and requires essentially the full attention of the test operator to time the filtration duration and volume measurements, monitor sample pressure and temperature, record data and perform calculations, and no quantitative PF or SDI values are available before the entire test is completed. An analysis response time of substantially less than 30 minutes would be highly desireable for the monitoring and adjustment of pretreatment performance for optimum particulate removal. Another major limitation of the ASTM test is that it is not recommended for waters with high plugging factors (>75% after 5 minutes' filtration) which prevents the method's application to characterize feed water quality in many existing RO applications. The test apparatus and procedures are better suited for a laboratory environment than for the field. Failure of the operator to carefully install very thin membrane filters, which are best handled only by tweezers, into a filter holder and imprecise purging of all air bubbles from the apparatus before each measurement often lead to measurement errors and data scatter.

Existing automated monitors developed to perform PF and SDI tests also have drawbacks. Operator-intensive procedures of the manual method have been replaced by automated handling of membrane filters in the form of tape rolls, such as that disclosed in U.S. Pat. No. 4,554,822, requiring complicated, relatively bulky mechanical equipment which is impractical for field use and too expensive for most practical RO applications. Because membrane filter tape is not a standard product it is difficult to obtain a reliable supply of consistent quality at a reasonable price. Moreover, although such monitors automate the measurement process and data reporting, they do not increase the amount of data per sample nor improve upon data analysis procedures of the manual method. The automated PF monitor still requires about 20 minutes to complete one test, provides no PF data prior to test completion, cannot accurately analyze samples where the PF is very high, and provides no information on filter-plugging profiles, reflected in the shape of graphs of filtration flow rate versus filtration duration.

Existing filtration methods for monitoring the quality of ultrapure water such as are disclosed in U.S. Pat. Nos. 4,765,963 and 4,786,473 are unsuitable for measuring PF or SDI for RO feed water, which is typically at least two orders of magnitude more concentrated in particulate matter and ions than is ultrapure water. Such ultrapure water analyzers monitor continuously for changes in minute concentrations of submicro-sized particles (colloids) using a very fine filter having, for example, pores 0.1 micron in diameter, which are typically operated continuously with the same filter for days. A 0.1 micron filter operated on typical RO feedwater at 30 psi doesn't permit either sufficient flow or a representative sample of large particulate matter therethrough to provide any meaningful, reproducible quantitative data on level of particulate matter present. Water sampling techniques of ultrapure water monitors do not maintain sufficiently turbulent flow during sampling to maintain particles greater than 1.0 micron in suspension without some of them settling out in the apparatus before reaching the filtration step, especially when flow rate drops as a result of high levels of filter plugging. The location of a mechanical pressure regulator containing small flow passages in the sample pipe upstream of the filter exerts a filtering effect on larger particles, and the regulators' capability to maintain constant pressure is severely impaired as the filtration flow rate approaches zero. Particulate matter previously settled out from prior samples in the apparatus can contaminate subsequent samples, resulting in erroneously high PF readings. The required manual installation of membrane filters in holders results in the same errors discussed above pertaining to manual methods of measuring PF and SDI.

There is therefore a clear need in the art for a simple, reliable, semi-automated device for accurately measuring the level of suspended particulate matter in water, and that is capable of quickly reporting reproducible results.

SUMMARY OF THE INVENTION

The present invention comprises apparatus for measuring the level of particulate matter in water, such as RO feedwater, containing particulates $\geq 0.2$ micron in diameter comprising:

(a) a sampling pipe for removing a sample of water from water containing particulate matter $\geq 0.2$ micron in diameter, the sampling pipe having an inlet and a first outlet and a second outlet, the inlet being in communication with the flow of feed water;

(b) pump means in communication with the inlet of the sampling pipe for pressurizing the sample of water and for delivering the same to the sampling pipe;

(c) means connected to the first outlet of the sampling pipe for maintaining water pressure within the sampling pipe at a constant value and for bleeding off a portion of the sample of water;

(d) filter means in communication with the second outlet of the sampling pipe for filtering said sample of water passing through said second outlet of the sampling pipe, the filter means being capable of filtering particulate matter from the sample of water and of permitting a water sample flow rate of at least 100 mL/min. at 30 psi and 25° C.;

(e) flow rate detecting means for continuously detecting the flow rate of the sample of water passing through the filter means and generating a corresponding output as a function of time; and (f) evaluating means coupled to the flow rate detecting means for determining at predetermined times PF and/or SDI of the sample of water passing through the flow rate detecting means.

DETAILED DESCRIPTION OF PREFERRED EMBODIMENTS

Figure 1:
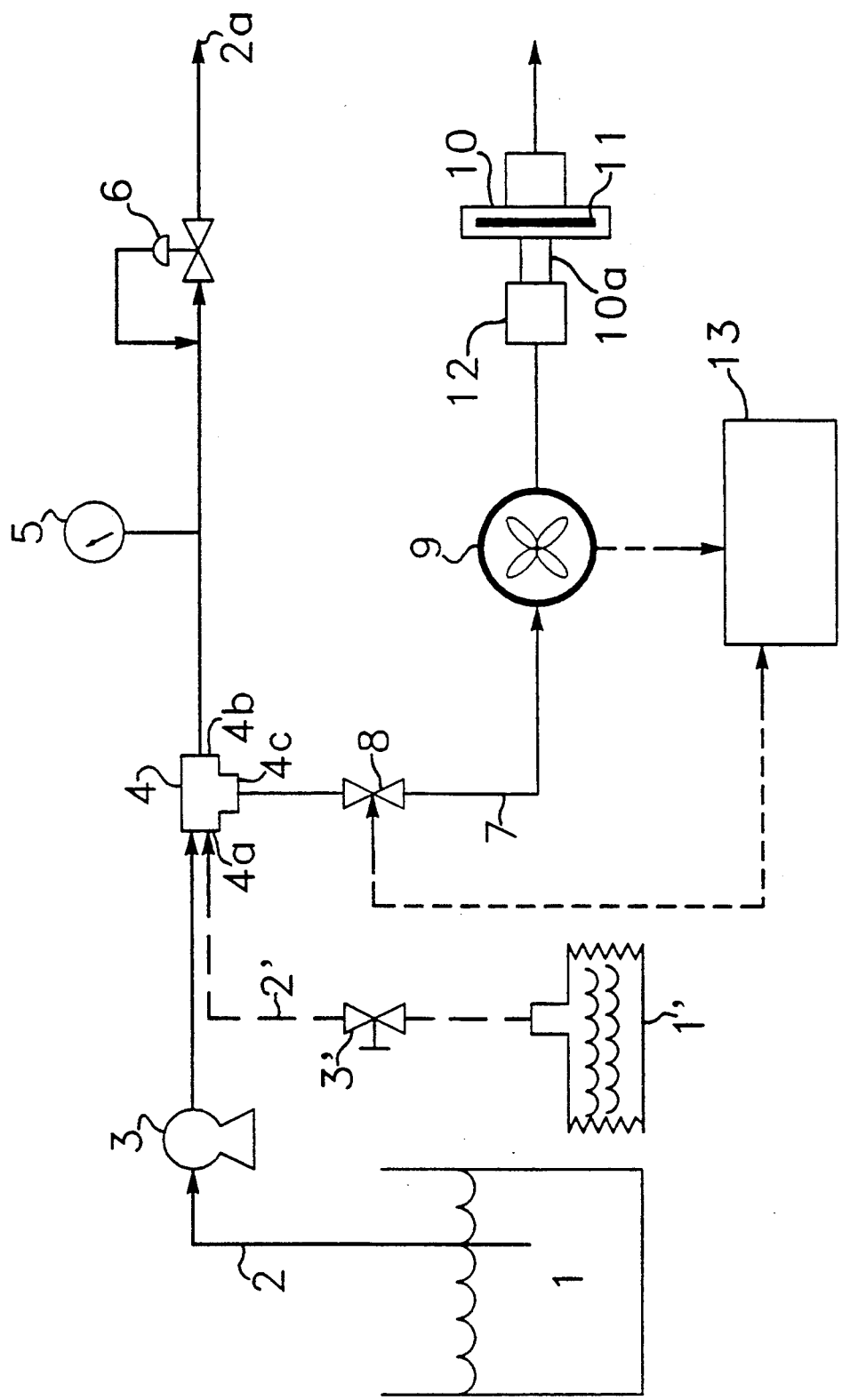
FIG. 1 is a schematic of an exemplary form of the apparatus of the present invention.

Referring to FIG. 1, there is schematically shown an exemplary preferred embodiment of the apparatus comprising a source 1 of water containing both smaller size and relatively larger size ($\geq 0.2$ micron in diameter) particulates, a sample line 2 connected to a pump 3 for pressurizing the sample of water and delivering it to a sampling Tee 4 having an inlet 4a, a first outlet 4b and a second outlet 4c. The source of water may be a reservoir 1 or a conduit such as a pipe 1'; when the latter is used, water therein is typically under pressure so that a pressure-reducing valve 3' is used instead of a pump. Pump 3 need not be in place as shown in the schematic, but may be further upstream, even somewhere in or a part of the source line 1, so long as it is capable of maintaining at least 30 psi positive pressure at the sampling Tee outlets 4b and 4c and at the filter element 11. The first outlet 4b is in fluid communication with a pressure gauge 5 and a combination back pressure regulator/bleed-off valve 6 for maintaining constant pressure in the outlets 4b and 4c of the sampling pipe and in the filter feed line 7. Water containing a representative portion of the particulate matter that was present in the water in sample line 2 is bled off through back pressure regulator/bleed-off valve 6 to drain at 2a. An on/off valve 8 is interposed between sampling pipe 4 and flowmeter 9, the latter being upstream from a filter housing 10 containing a filter element 11. The filter housing 10 preferably has a male member 10a that matingly engages a female member 12 in a friction and bayonet fit allowing quick locking connection and disconnection of the housing from filter feed line 7. Flowmeter 9 generates data reflective of flow rates (Q) of the sample of water therethrough and generates output comprising such flow rates both at the beginning of the test ($Q_O$) and at a predetermined later time($Q_t$), the output being reported to a data acquisition and control system (DAC) 13 that is operatively coupled to the flowmeter 9. The flowmeter 9 may also generate a signal to trigger and/or stop a clock in DAC 13 to monitor and record the duration T of the test. (Alternately, the on/off valve 8 may be operatively coupled to DAC 13 to generate the same data.) DAC 13 is capable of calculating PF and/or SDI from these values and of recording, and displaying them by use of the equations $$PF = (1 - Q_t/Q_O) \times 100$$

$$SDI = PF/T$$

where T is the duration in minutes of the test.

In operation, a representative sample of siltor particulate-containing water is drawn off from the water to be tested and fed to the split stream sampling pipe 4, where a first portion exits outlet 4b and is bled off by back pressure regulator/bleed-off valve 6 and drained at 2a. A second portion of the sample exits outlet 4c and flows through flowmeter 9 and thence to filter module 10 and through filter element 11.

There are several advantages offered by the apparatus of the present invention. The use of a back pressure-type regulator and its location in a sidestream apart from the filter eliminates the impact on PF/SDI results of the filtering-out effect of particles in water passing through small passageways of the regulator. The bleed flow exhausted from the back pressure regulator maintains turbulent flow in the entering sample line(s) whereby representative sampling of even larger sizes of particulate matter is maintained without such particulate matter settling out. When the filter is located downstream of the flow meter faster and easier filter installation is possible because only the inlet of the filter needs to be connected and any air bubbles can be readily purged prior to operation.

Collection of continuous filtration flow and time data and its analysis on-line provides several additional advantages. Initial filtration flow representative of the individual filter prior to any plugging from particulate matter may be ascertained by projecting the initial flow-versus-time trend back to zero time, which information is useful for characterizing and testing the quality of a given filter. Following each subsequent flow measurement, this initial rate may be used to calculate a PF value that is immediately available to provide and display contemporaneous test results. PF and SDI values are available after only 5 minutes or less of test time, and on demand. Water samples which cause 75% PF in less than 5 minutes, and therefore cannot be evaluated quantitatively using conventional prior technology, may be accurately analyzed for their SDI using the present invention. Lower plugging samples which normally would require a 15 minute test period can be accurately analyzed with 5 minutes worth of data obtained with the present apparatus. Optional multiple automated valves (e.g., solenoid valves) and filters allow a number of samples to be analyzed sequentially over time and the data stored without operator attention. Even without multiple valves and filters, the apparatus of the present invention can analyze four times as many samples in the same time period as conventional manual methods. The present invention may also be in a portable configuration where it may be operated on test samples in the field.

EXAMPLES 1–126

Apparatus of substantially the same arrangement shown in FIG. 1 was used to test three sources of pretreated RO feedwater originating from Chesapeake Bay. Samples were taken from two different post-pretreatment filtration points from each of three water purification RO systems and both PF and SDI for the samples were measured. The pump used was a Model No. 120 (Micropump Corporation of Concord, Calif.), the pressure gauge a Model No. J8046 (Marsh Instrument Company of Hastings, Nebr.), and the back pressure regulator a Conoflow GH30 Series (IFF Fluid Technology Corporation of St. George, S.C.). The flowmeter comprised a Signet MK 2502 Low Flow Sensor and a MK 514 Signal Conditioner (both from George Fisher Signet, Inc. of Tustin, Calif.), while the filter module for each test was a Millex HA (Millipore Corporation of Bedford, Mass.) containing a Millipore 0.45 micron cellulose acetate membrane filter element, the module being connected to the filter feed line by a Luer-Lok ® connector. The DAC comprised a Keithley Model 570 Measurement and Control Center (Keithley Instrument, Inc., of Cleveland, Ohio) coupled with a Compaq Portable III Microcomputer. Measurement and control software was written in QuickBASIC Version 4.5.

The test was run 126 times at 30 psi constant pressure at temperatures ranging from 27° C. to 29° C., which gave an initial flow rate ($Q_O$) of from 245 to 453 mL/min. on actual RO feedwater, over a total period of 21 days. Operation was trouble-free with no performance errors. For 110 of the runs, definitive SDI results were achieved in less than 5 minutes, which consisted of samples where PF exceeded 75% in less than 5 minutes. Current manual and automatic PF methods would not have been able to produce any quantitive PF/SDI results for these 110 samples because of the limitations in the frequency and response time of their flow measurement capability involving the timing of filtrate volume collection after 5, 10 or 15 minutes of filtration. All of the required analyses each day were completed in 2 hours' total time by one person; had the same analyses been conducted with manual SDI/PF tests, it is estimated that at least 8 hours per day would have been required.

EXAMPLES 127-131

Figure 2:
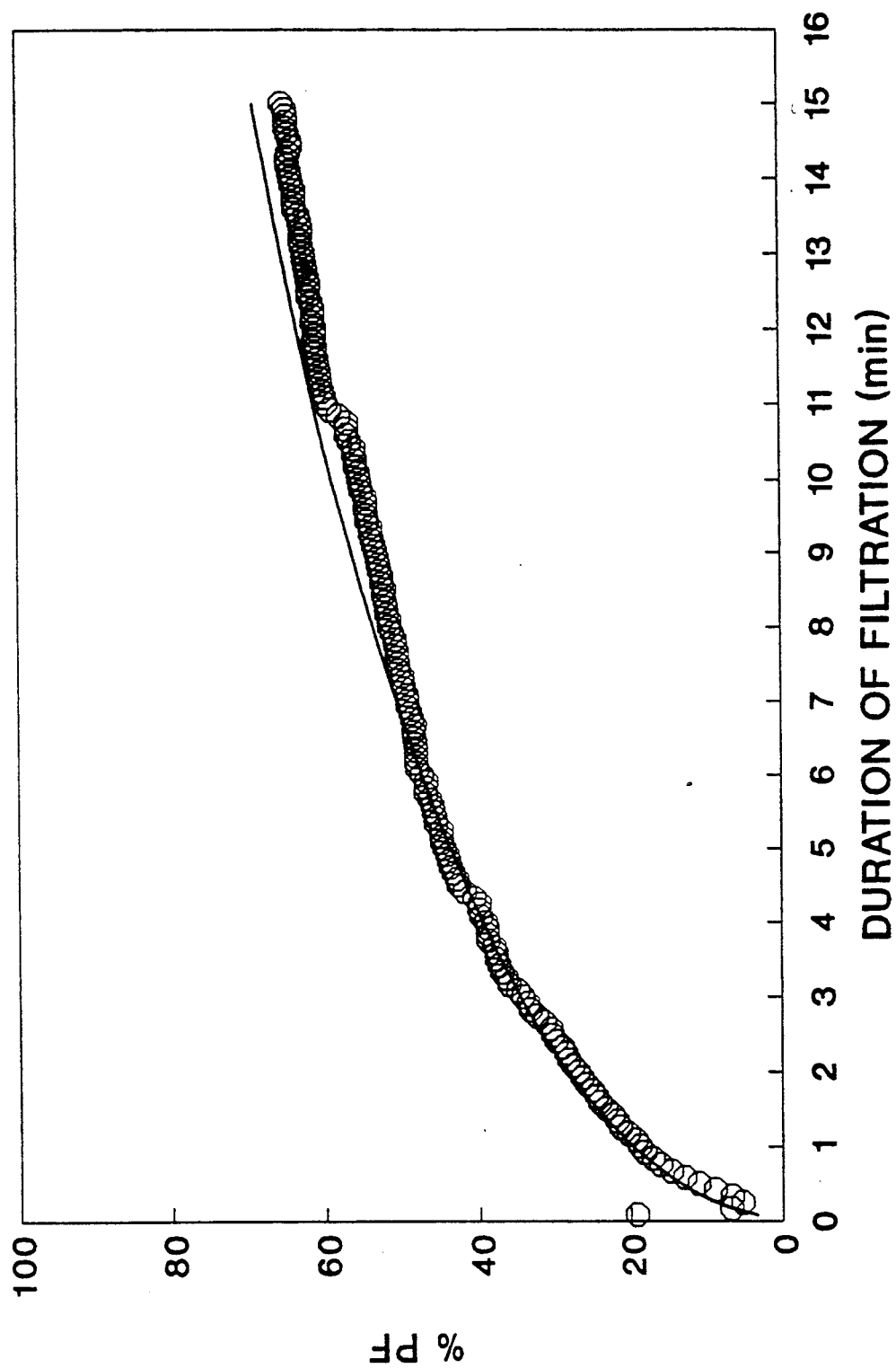
FIG. 2 is a graph showing operation of the apparatus of the invention and its capability of predicting PF from tests of very short duration.

The capability to shorten the analysis time for water samples in cases where PF is <75% after five minutes, and thus to successfully operate PF on the basis of short duration tests, was demonstrated by tests described as follows. The test source was tap water pretreated by cartridge filters, which represents one widely-used type of RO feedwater source for industrial use. The test equipment and pressure were substantially the same as in Examples 1–126. Curve shape analysis of early flow-versus-time data was used to fit model equations which successfully predicted the shape of the PF curve for the full test duration as demonstrated by typical data shown in FIG. 2. The solid curve in FIG. 2 is based solely on a blocking filtration model fit to data for the first 5 minutes of the test but projected to 15 minutes, and the circles are for actual data for the test continued for a full 15-minute duration. In five tests, where the final PF values ranged from 15 to 72%, there was agreement within 3% between the 15-minute PF's predicted by the apparatus based on the initial 5 minutes' worth of data and the actual PF data observed after 15 minutes of filtration.

EXAMPLES 132-136

The capability to operate with 0.22 micron pore size filters was demonstrated in five tests on RO feed water using the same apparatus depicted in FIG. 1. The water samples were tested at a desalination plant in Arizona, which treats saline agriculture drainage water. The five samples tested had been pretreated by partial lime softening and media filtration. In addition, two of the five samples had undergone cartridge filtration. Operation on the samples with Millex GS and GV filter modules (Millipore Corporation) containing filter elements with 0.22 micron pore size ratings gave initial flow rates ($Q_O$) ranging from 109 to 172 mL/min and provided accurate 15-minute PF values ranging from 6.3% to 16.6% with water temperatures from 26° to 30° C.

COMPARATIVE EXAMPLE

Figure 3:
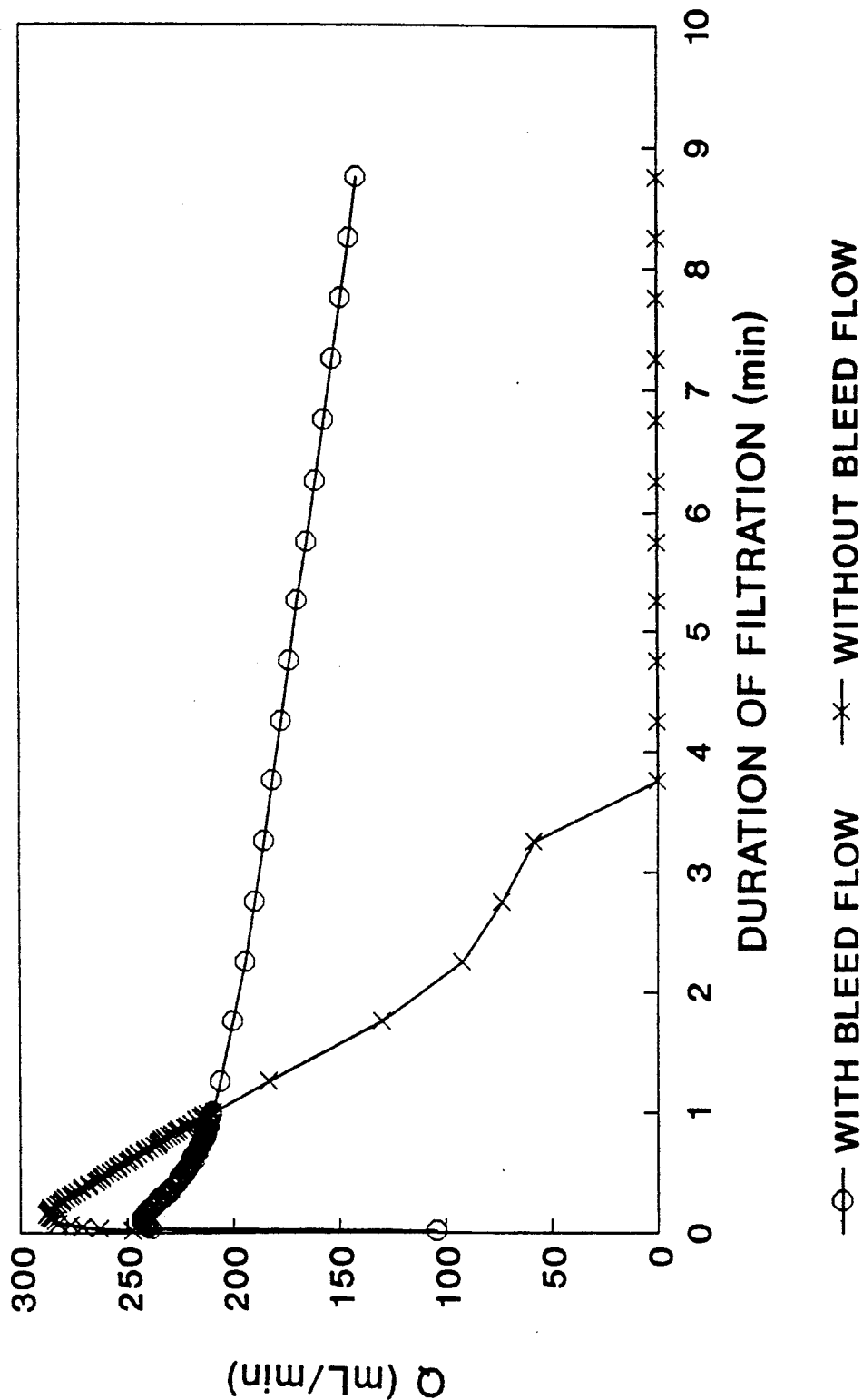
FIG. 3 is a graph showing operation of the apparatus of the invention with and without the bleedoff feature.

Several tests of the same water were run to show the benefits of bleed flow and placing pressure regulation in a branch stream separate from the filtration and flow measurement. Substantially the same apparatus as described in the Examples above was used but pressure was controlled by a regulating valve located in sample line 2 just prior to sampling pipe 4. The results, shown in FIG. 3, demonstrated that the filter blinded prematurely (in about four minutes) when bleed flow was turned off. This behavior was attributed in large part to contamination of sample water by resuspended particles that had settled out from previous samples in the apparatus under low flow conditions caused by high filter plugging due to large particulate matter and without any bleed flow to maintain the particles in suspension. The premature filter plugging shown in FIG. 3 occurred despite repeated efforts to flush the system out with clean water between tests and was eventually only eliminated through resumption of bleed flow.

Figure 4:
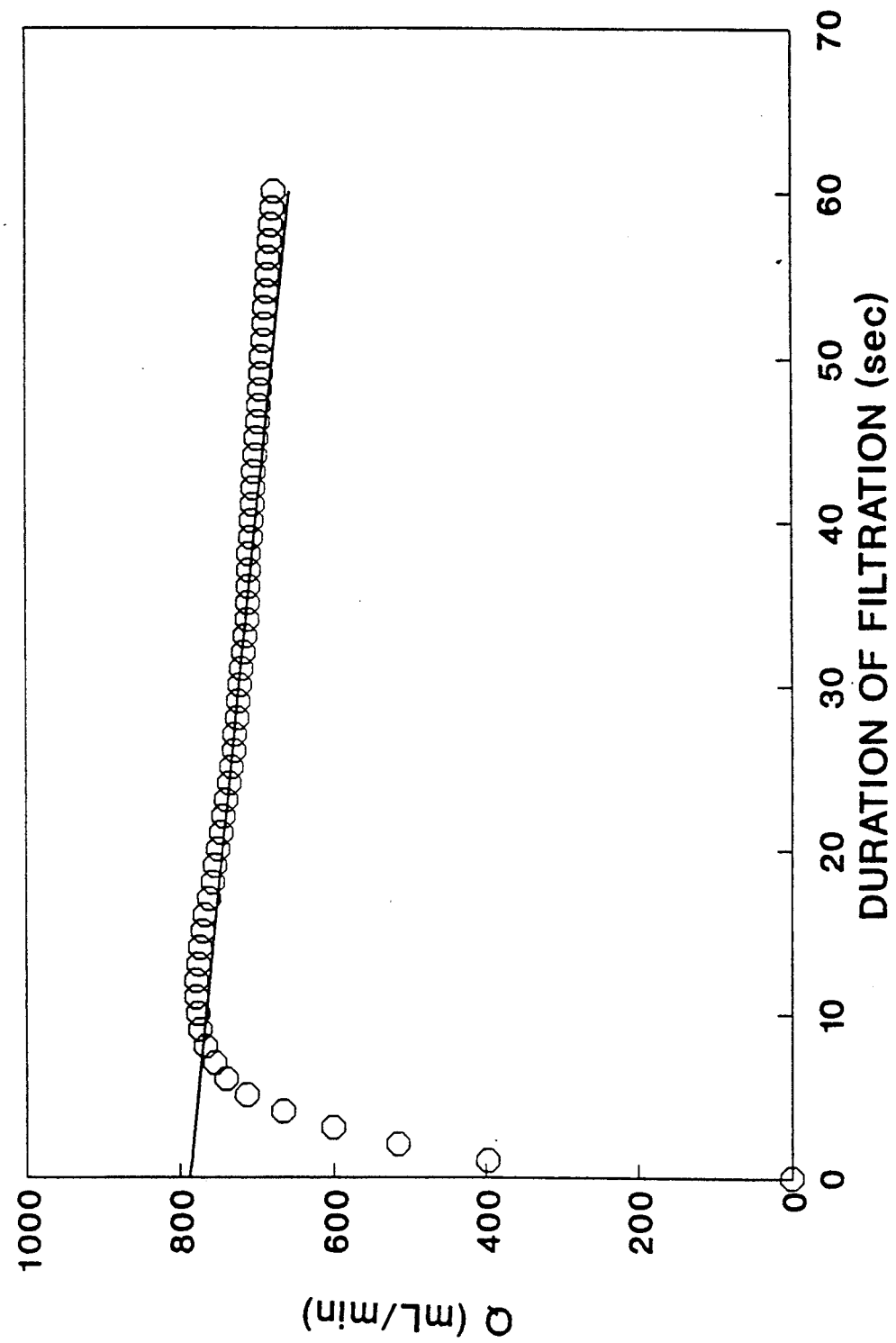
FIG. 4 is a graph showing operation of the apparatus of the present invention and its capability of ascertaining initial filtration or flow rates based upon tests of very short duration.

The apparatus of the present invention is also capable of estimating initial filtration flow rate ($Q_O$) through a filter. FIG. 4 shows how the initial flow rate ($Q_O$) versus time in the range of 20 to 40 seconds is fit by linear regression (the method of least squares) and then projected back to zero time as shown by the solid line fit. The value of ($Q_O$) thus obtained is more representative of a filtration flow prior to the occurrence of plugging than conventional practice involving the direct determination of time to collect an initial sample volume during which plugging is already under way and can be as much as 25% for a high PF water before completion of the initial volume measurement. This $Q_O$ value may be used to calculate PF in each subsequent on-line PF test and may further be used to characterize and standardize filters.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. Apparatus for measuring the level of particulates in water containing particulates $\geq 0.2$ micron in diameter comprising:
    (a) a sampling pipe for removing a sample of water from water containing particulates, said sampling pipe having an inlet and a first outlet and a second outlet, the inlet being in communication with said flow of water;
    (b) pump means in communication with the inlet of said sampling pipe for pressurizing said sample of water and for delivering the same to said sampling pipe;
    (c) back pressure regulator means connected to the first outlet of said sampling pipe for maintaining water pressure within said sampling pipe at a constant value and for continuously bleeding off a portion of said sample of water;
(d) filter means in communication with the second outlet of said sampling pipe for filtering said sample of water passing through said second outlet of said sampling pipe, said filter means being capable of filtering particulate matter from said sample of water and of permitting a water sample flow rate of at least 100 mL/min. at 30 psi and 25° C.;
(e) flow rate detecting means for continuously detecting the flow rate of said sample of water passing through said filter means and generating a corresponding output as a function of time; and
(f) evaluating means coupled to said flow rate detecting means for determining at predetermined times the plugging factor and/or the silt density index of said sample of water passing through said flow rate detecting means.

2. Apparatus of claim 1, including means for recording and means for displaying calculations utilizing the plugging factor and/or silt density index.

3. Apparatus of claim 1, including a valve interposed between said pump means and said flow rate detecting means.

4. Apparatus of claim 1 wherein said filter means is disposed at said second outlet of said sampling pipe and said flow rate detecting means is upstream of said filter means.

5. Apparatus of claim 1 wherein said filter means comprises a filter having pores substantially 0.45 micron in diameter.

* * * * *